US010138257B2

(12) United States Patent
Cano et al.

(10) Patent No.: US 10,138,257 B2
(45) Date of Patent: Nov. 27, 2018

(54) TRANSITION METAL COMPLEXES, PRODUCTION AND USE THEREOF

(71) Applicant: ExxonMobil Chemical Patents Inc., Baytown, TX (US)

(72) Inventors: David A. Cano, Houston, TX (US); Crisita Carmen H. Atienza, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/666,085

(22) Filed: Aug. 1, 2017

(65) Prior Publication Data

US 2018/0057513 A1 Mar. 1, 2018

Related U.S. Application Data

(60) Provisional application No. 62/380,162, filed on Aug. 26, 2016.

(51) Int. Cl.

| C07F 7/00 | (2006.01) |
| C08F 210/16 | (2006.01) |
| C07F 9/572 | (2006.01) |
| C08F 4/659 | (2006.01) |
| C08F 2/04 | (2006.01) |
| C07F 7/10 | (2006.01) |

(52) U.S. Cl.
CPC ............. *C07F 7/00* (2013.01); *C07F 9/5728* (2013.01); *C08F 210/16* (2013.01); *C08F 4/659* (2013.01); *C08F 4/65908* (2013.01); *C08F 4/65912* (2013.01)

(58) Field of Classification Search
CPC . C07C 7/0812; C07C 7/0818; C08F 4/65908; C08F 4/65912
USPC .......................................................... 556/22
See application file for complete search history.

(56) References Cited

U.S. PATENT DOCUMENTS

| 8,937,137 B2 | 1/2015 | Holtcamp et al. |
| 8,952,114 B2 | 2/2015 | Giesbrecht et al. |
| 8,957,171 B2 | 2/2015 | Giesbrecht et al. |
| 8,957,172 B2 | 2/2015 | Giesbrecht et al. |
| 9,045,568 B2 | 6/2015 | Giesbrecht et al. |
| 9,150,676 B2 | 10/2015 | Kol et al. |
| 9,193,813 B2 | 11/2015 | Kol et al. |
| 9,200,099 B2 | 12/2015 | Kol et al. |
| 9,200,100 B2 | 12/2015 | Kol et al. |
| 9,290,589 B2 | 3/2016 | Evans et al. |
| 9,365,661 B2 | 6/2016 | Giesbrecht et al. |
| 9,382,349 B2 | 7/2016 | Harrington et al. |
| 9,464,148 B2 | 10/2016 | Giesbrecht et al. |
| 2015/0158958 A1 | 6/2015 | Harrington et al. |
| 2015/0337058 A1 | 11/2015 | Giesbrecht et al. |

OTHER PUBLICATIONS

Qi et al., "Titanium and Zirconium Complexes with Novel Phenoxyphosphinimine Ligands", Journal of Organometallic Chemistry, Elsevier—Sequoia S. A. Lausanne, CH, Sep. 1, 2005, vol. 690, No. 17, pp. 3946-3950.
Wang et al., "Ethylene Oligomerization by Salen-type Zirconium Complexes to Low-carbon Linear [alpha]-olefins", Journal of Catalysis, Dec. 10, 2003, vol. 220, No. 2, pp. 392-398.
Cao et al., "Phosphasalen Yttrium Complexes: Highly Active and St3ereoselective Initiators for Lactide Polymerization", Inorganic Chemistry, Feb. 20, 2012, vol. 51, No. 4, pp. 2157-2169.
Bakewell et al., "Scandium and Yttrium Phosphasalen Complexes as Initiators for Ring-Opening Polymerization of Cyclic Esters," Inorganic Chemistry, 2015, vol. 54, No. 5, pp. 2204-2212.
Bakewell et al., "Yttrium Phosphasalen Initiators for rac-Lactide Polymerization," Organometallics, 2013, vol. 32, No. 5, pp. 1475-1483.
Bakewell et al., "Yttrium Phosphasalen Initiators for rac-lactide Polymerization: Excellent Rates and High Iso-Slectivities," Journal of the American Chemical Society, 2012, No. 134, vol. 51, pp. 20577-20580.
Bakewell et al., "Metal-Size Influence in Iso-Selective Lactide Polymerization," Angewandte Communication, 2014, No. 53, pp. 9226-9230.
Buchard et al., "Iminophosphorane Neodymium(III) Complexes as Efficient Initiators for Lactide Polymerization," Organometallics, 2010, vol. 29, No. 13, pp. 2892-2900.
Buchard et al., "First Neodymium(III) Alkyl-carbine Complex Based on bis(iminophosphoranyl) ligands," Dalton Transactions, 2009, pp. 10219-10222.
Cao et al., "Pd(II) and Ni(II) complexes feature a "phosphasalen" ligand: synthesis and DFT study," Dalton Transactions, 2011, vol. 40, pp. 10029-10037.
Cheisson et al., "Nickel Complexes Featuring Iminophosphorane-Phenoxide Ligands for Catalytic Ethylene Dimerization," Organometallics, 2014, vol. 33, No. 21, pp. 6193-6199.

(Continued)

*Primary Examiner* — Fred M Teskin

(57) ABSTRACT

Phosphasalen transition metal complexes are disclosed for use in alkene polymerization to produce polyolefins. The transition metal complexes are represented by the formula:

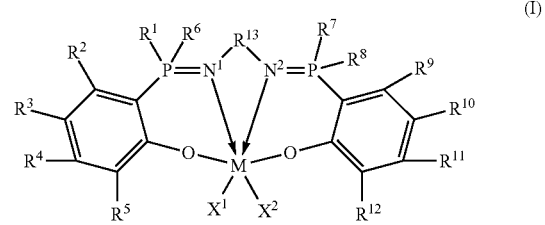

wherein M is a Group 4 metal; each of $X^1$ and $X^2$ is a univalent group, such as halogen or benzyl; each of $R^1$, $R^2$, $R^3$, $R^4$, $R^5$, $R^6$, $R^7$, $R^8$, $R^9$, $R^{10}$, $R^{11}$, and $R^{12}$ is, independently, hydrogen, a substituted or unsubstituted $C_1$-$C_{40}$ hydrocarbyl radical, etc.; and $R^{13}$ is a divalent $C_1$-$C_{20}$ hydrocarbyl radical or divalent substituted $C_1$-$C_{20}$ hydrocarbyl radical comprising a portion that comprises a linking backbone comprising from 2 to 18 carbon atoms linking $N^1$ and $N^2$.

37 Claims, No Drawings

(56) References Cited

OTHER PUBLICATIONS

Hodgson et al., "A Series of Bis(thiophosphinic amido)yttrium Initiators for Lactide Ring-Opening Polymerization," Macromolecules, 2008, vol. 41, No. 22, pp. 8603-8607.

Hodgson et al., "Yttrium(III) Complex as a Highly Active Catalyst for Lactide Polymerization," Journal of Polymer Science Part A: Polym. Chem., Rapid Communication, 2006, vol. 44, pp. 6646-6651.

Platel et al., "A Series of Bis(phosphinic)diamido Yttrium Complexes as Initiators for Lactide Polymerization," Inorganic Chemistry, 2008, vol. 47, No. 15, pp. 6840-6849.

Platel et al., "Synthesis and Characterization of a Series of Bis(oxo/thiophosphinic) diamido Yttrium Complexes and Their Application as Initiators for Lactide Ring-Opening Polymerization," Organometallics, 2007, vol. 26, No. 20, pp. 4955-4963.

Platel et al., "Stereocontrolled lactide polymerization determined by the nuclearity of the yttrium initiator," Chem. Commun., 2009, pp. 4115-4117.

Cao et al., "A Tetracoordinated Phosphasalen Nickel (III) Complex," Angewandte Chemie International Edition, 2013, vol. 53, No. 5, pp. 1368-1372.

TRANSITION METAL COMPLEXES, PRODUCTION AND USE THEREOF

PRIORITY CLAIM

This application claims priority to and the benefit of U.S. Ser. No. 62/380,162, filed Aug. 26, 2016 and is incorporated by reference in its entirety.

FIELD OF INVENTION

The invention relates to phosphasalen transition metal complexes and intermediates and processes for use in making such phosphasalen complexes. The transition metal complexes may be used as catalysts for alkene polymerization processes.

BACKGROUND OF INVENTION

Olefin polymerization catalysts are of great use in industry. Hence, there is interest in finding new catalyst systems that increase the commercial usefulness of the catalyst and allow the production of polymers having improved properties.

Salen and or Salalen complexes have been used as transition metal components in the polymerization of alkenes, see, for example, U.S. Pat. Nos. 9,382,349; 9,464,148; 9,290,589; 9,193,813; 8,957,171; 8,957,172; 8,952,114; 9,045,568; 9,365,661; 8,937,137; 9,150,676; 9,200,099; and 9,200,100.

Inorganic Chemistry 2015, 54, 2204-2212 and Angewandte Chemie, International Edition 2014, 53, 9226-9230 describe the use of phosphasalen complexes as lactide polymerization catalysts.

Journal of Organometallic Chemistry 2006, 690, 3946-3950 describes the use of phenoxy-phosphinimine titanium and zirconium complexes as ethylene polymerization catalysts.

Other references of interest include: Organometallics (2013), 32(5), 1475-1483; Journal of the American Chemical Society 2012, 134, 20577-20580; Inorganic Chemistry 2012, 51, 2157-2169; Dalton Trans. 2011, 40, 10029-10037; Dalton Trans. 2009, 46, 10219-10222; Organometallics 2010, 29 (13), 2892-2900; Inorg. Chem. 2008, 47 (15), 6840-6849; Chem. Commun. 2009, 27, 4115-4117; Macromolecules 2008, 41 (22), 8603-8607; Organometallics 2007, 26 (20), 4955-4963; Polym. Sci., Part A: Polym. Chem. 2006, 44 (22), 6646-6651; Organometallics 2014, 33, 6193-6199.

There still is need for new catalyst compounds to widen the range of catalyst complexes available for superior performance in alkene polymerization. The performance may be varied with respect to the amount of polymer produced per amount of catalyst (generally referred to as the "activity") under the prevailing polymerization conditions; the molecular weight and molecular weight distribution achieved at a given temperature; and/or the placement of higher alpha-olefins in terms of the degree of stereoregular placement.

Further, there is a need in the art for new catalysts with high activity that can produce ethylene and or propylene polymers.

SUMMARY OF INVENTION

This invention relates to novel transition metal complexes having phosphasalen ligands. This invention also relates to transition metal complexes represented by the formula (I):

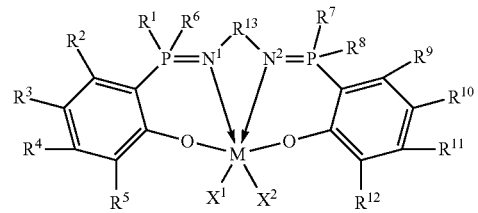

wherein each solid line represents a covalent bond, and an arrow represents a dative bond;
wherein M is a Group 4 metal;
$N^1$ and $N^2$ are nitrogen;
O is oxygen;
P is phosphorus;
each of $X^1$ and $X^2$ is, independently, a univalent $C_1$ to $C_{20}$ hydrocarbyl radical, a functional group comprising elements from Groups 13 to 17, or $X^1$ and $X^2$ join together to form a $C_4$ to $C_{62}$ cyclic, polycyclic or heterocyclic ring structure;
each of $R^1$, $R^2$, $R^3$, $R^4$, $R^5$, $R^6$, $R^7$, $R^8$, $R^9$, $R^{10}$, $R^{11}$, and $R^{12}$, is, independently, hydrogen, a $C_1$-$C_{40}$ hydrocarbyl radical, a functional group comprising elements from Groups 13 to 17, two or more of $R^1$, $R^2$, $R^3$, $R^4$, $R^5$, $R^6$, $R^7$, $R^8$, $R^9$, $R^{10}$, $R^{11}$, and $R^{12}$ optionally join together to form a $C_4$ to $C_{62}$ cyclic or polycyclic or heterocyclic ring structure, or a combination thereof; and
$R^{13}$ is a divalent $C_1$-$C_{20}$ hydrocarbyl radical or divalent substituted $C_1$-$C_{20}$ hydrocarbyl radical comprising a portion that comprises a linking backbone comprising from 1 to 20 carbon atoms linking $N^1$ and $N^2$.

This invention further relates to processes to make the above complexes, processes to make intermediates for the above complexes and methods to polymerize olefins using the above complexes.

DETAILED DESCRIPTION

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

As used herein, Me is methyl, Et is ethyl, Bu is butyl, t-Bu and ᵗBu are tertiary butyl, Pr is propyl, iPr and ⁱPr are isopropyl, Cy is cyclohexyl, THF (also referred to as thf) is tetrahydrofuran, Bn is benzyl, and Ph is phenyl. Room temperature is 23° C., unless otherwise stated.

Unless otherwise indicated, the term "substituted" generally means that a hydrogen of the substituted species has been replaced with a different atom or group of atoms. For example, methyl-cyclopentadiene is cyclopentadiene that has been substituted with a methyl group. Likewise, picric acid can be described as phenol that has been substituted with three nitro groups, or, alternatively, as benzene that has been substituted with one hydroxy and three nitro groups.

The terms "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "hydrocarbyl radical" is defined to be $C_1$-$C_{100}$ radicals, that may be linear, branched, cyclic, or polycyclic, and when cyclic, aromatic or non-aromatic.

A substituted hydrocarbyl radical is a hydrocarbyl radical in which at least one hydrogen atom of the hydrocarbyl radical has been substituted with at least one functional group such as F, CL, Br, I, C(O)R*, C(O)NR*$_2$, C(O)OR*, NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like (where R* is independently a hydrogen or hydrocarbyl radical, and two or more R* may join together to form a substituted or unsubstituted saturated, partially unsaturated or aromatic cyclic or polycyclic ring structure), or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

The term "complex," may also be referred to as catalyst precursor, precatalyst, catalyst, catalyst compound, transition metal compound, or transition metal complex. These words are used interchangeably. Activator and cocatalyst are also used interchangeably.

In the formulas presented herein a solid line represents a covalent bond and an arrow represents a dative bond.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

For purposes herein an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have a "propylene" content of 35 wt % to 55 wt %, it is understood that the mer unit in the copolymer is derived from propylene in the polymerization reaction and said derived units are present at 35 wt % to 55 wt %, based upon the weight of the copolymer. A higher α-olefin is defined to be an α-olefin having 3 or more carbon atoms. For the purposes of this disclosure ethylene is considered an alpha-olefin.

For purposes herein a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) reported in g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise, heteroaryl means an aryl group where a ring carbon atom (or two or three ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring. A substituted heterocyclic ring is a heterocyclic ring in which at least one hydrogen atom of the heterocyclic ring has been substituted with a hydrocarbyl group, a substituted hydrocarbyl group or a functional group such as F, Cl, Br, I, C(O)R*, C(O)NR*$_2$, C(O)OR*, NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like (where R* is independently a hydrogen or hydrocarbyl radical, and two or more R* may join together to form a substituted or unsubstituted saturated, partially unsaturated or aromatic cyclic or polycyclic ring structure).

As used herein, the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

This invention relates to phosphalen catalyst compounds, as described herein and catalyst systems comprising such catalyst compound and activator.

This invention also relates to a process comprises contacting one or more olefins with a catalyst system according to any one or combination of embodiments disclosed herein at a temperature, a pressure, and for a period of time sufficient to produce a polyolefin. In an embodiment according to the invention, the catalyst compound is disposed on a support.

Catalyst Compounds

This invention relates to transition metal complexes represented by the formula (I):

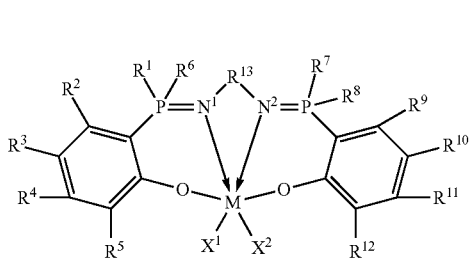

(I)

wherein each solid line represents a covalent bond and an arrow represents a dative bond;
wherein M is a Group 4 metal;
$N^1$ and $N^2$ are nitrogen;
P is phosphorus;
O is oxygen;
each of $X^1$ and $X^2$ is, independently, a univalent $C_1$ to $C_{20}$ hydrocarbyl radical, a functional group comprising elements from Groups 13 to 17, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, and $R^{12}$ is, independently, hydrogen, a $C_1$-$C_{40}$ hydrocarbyl radical, a functional group comprising elements from Groups 13 to 17, two or more of $R^1$, $R^2$, $R^3$, $R^4$, $R^5$, $R^6$, $R^7$, $R^8$, $R^9$, $R^{10}$, $R^{11}$, and $R^{12}$ optionally join together to form a $C_4$ to $C_{62}$ cyclic or polycyclic or heterocyclic ring structure, or a combination thereof; and
$R^{13}$ is a divalent $C_1$-$C_{20}$ hydrocarbyl radical or divalent substituted $C_1$-$C_{20}$ hydrocarbyl radical comprising a portion that comprises a linking backbone comprising from 2 to 18 carbon atoms linking $N^1$ and $N^2$.

In an embodiment according to the invention, M is Hf. In another embodiment according to the invention, M is Ti. In another embodiment according to the invention, M is Zr.

In an embodiment, according to the invention, $X^1$ and $X^2$ are independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido, preferably each of $X^1$ and $X^2$ is, independently, a halogen or a benzyl radical.

In any embodiment, according to the invention, $R^{13}$ is a divalent $C_1$-$C_{20}$ hydrocarbyl radical or divalent substituted $C_1$-$C_{20}$ hydrocarbyl radical comprising a portion that comprises a linking backbone comprising from 1 to 20 carbon atoms linking $N^1$ and $N^2$.

In any embodiment, according to the invention, $R^{13}$ is a divalent $C_1$ to $C_{12}$ aliphatic radical (preferably $C_{2-8}$ aliphatic radical) which may be cyclic, branched or linear. Preferably, $R^{13}$ is selected from the group consisting of methylene, ethylene, propylene, butylene, pentylene, hexylene, heptylene, octytlene, nonylene, decylene, undecylene, doecylene, cyclohexylene, cycloheptylene cyclooctylene, phenylene, dimethylphenylene and isomers thereof.

In an embodiment according to the invention, each of $R^1$, $R^2$, $R^3$, $R^4$, $R^6$, $R^7$, $R^8$, $R^9$, $R^{10}$, and $R^{11}$, is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^1$ to $R^{12}$ groups may join together to form a $C_4$ to $C_{62}$ cyclic or polycyclic ring structure, or a combination thereof, preferably each of $R^1$, $R^2$, $R^3$, $R^4$, $R^6$, $R^7$, $R^8$, $R^9$, $R^{10}$, and $R^{11}$, is, independently, a $C_1$-$C_{20}$ hydrocarbyl radical, preferably a $C_1$-$C_{20}$ alkyl or aromatic radical, preferably each of $R^1$, $R^2$, $R^3$, $R^4$, $R^6$, $R^7$, $R^8$, $R^9$, $R^{10}$, and $R^{11}$, is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, adamantyl, substituted adamantyl, cyclohexyl, substituted cyclohexyl phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, and substituted indenyl.

In an embodiment according to the invention, $R^5$ and $R^{12}$ is, independently, a hydrogen, a $C_1$-$C_{40}$ hydrocarbyl radical, a $C_1$-$C_{40}$ substituted hydrocarbyl radical, a heteroatom or a heteroatom-containing group, preferably each of $R^5$ and $R^{12}$ is, independently, a $C_1$-$C_{20}$ hydrocarbyl radical, preferably a $C_1$-$C_{20}$ alkyl or aromatic radical, preferably each of $R^5$ and $R^{12}$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, adamantyl, substituted adamantyl, cyclohexyl, substituted cyclohexyl phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, and substituted indenyl.

In an embodiment according to the invention, at least one or both of $R^5$ and $R^{12}$ is, independently, a bulky functional group radical having a molecular size greater than or equal to a molecular size of an isopropyl functional group radical.

In an embodiment according to the invention, at least one (alternately, two, three, or four) of $R^3$, $R^5$, $R^{10}$, and $R^{12}$ is, independently, a substituted or unsubstituted aliphatic radical having four carbons or more, a substituted or unsubstituted alicyclic radical having six carbons or more (preferably 6 to 20 carbon atoms), or a combination thereof.

In an embodiment according to the invention, one or both of $R^5$ and $R^{12}$ is, independently, methyl, tert-butyl, adamantyl, substituted adamantyl, cyclohexyl, substituted cyclohexyl, phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, and substituted indenyl.

In an embodiment according to the invention, one or both of $R^5$ and $R^{12}$ is, independently, a substituted or unsubstituted carbazolyl radical.

For purposes herein, a carbazole radical or substituted carbazole radical is represented by the formula:

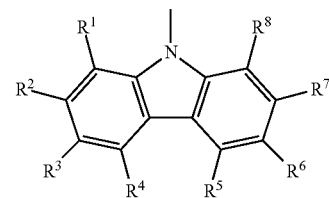

wherein each $R^1$ through $R^8$ is, independently, a hydrogen, a $C_1$-$C_{40}$ hydrocarbyl radical, a functional group comprising elements from Group 13 to 17, or two or more of $R^1$ to $R^8$ may independently join together to form a $C_4$ to $C_{62}$ cyclic or polycyclic ring structure, or a combination thereof.

In an embodiment according to the invention, one or both of $R^5$ and $R^{12}$ is, independently, a substituted or unsubstituted fluorenyl radical.

A substituted or unsubstituted fluorenyl radical is represented by the formula:

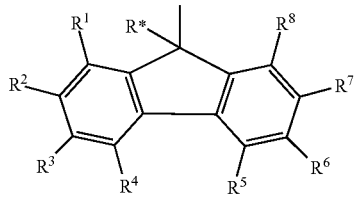

wherein each $R^1$ through $R^8$ is, independently, a hydrogen, a $C_1$-$C_{40}$ hydrocarbyl radical, a functional group comprising elements from Group 13 to 17, or two or more of $R^1$ to $R^8$ may independently join together to form a $C_4$ to $C_{62}$ cyclic or polycyclic ring structure, or a combination thereof; R* is a hydrogen, a $C_1$-$C_{40}$ hydrocarbyl radical, a substituted $C_1$-$C_{40}$ hydrocarbyl radical (preferably R* is methyl, phenyl, or substituted phenyl).

In an embodiment according to the invention, M is Ti, Zr, or Hf, each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, and wherein:
i) each of $R^3$ and $R^{10}$ is independently hydrogen, methyl, tert-butyl or isopropoxy; and
ii) each of $R^5$ and $R^{12}$ is independently tert-butyl radical, adamantyl, substituted adamantyl, cyclohexyl, substituted cyclohexyl phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, substituted indenyl.

In embodiments according to the invention, the catalyst compound is represented by the formula:

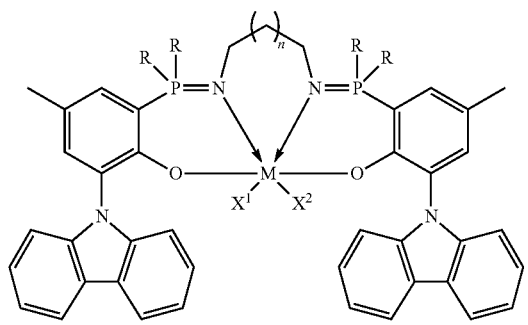

wherein M is Ti, Zr, or Hf, preferably Hf or Zr; each R is independently phenyl or isopropyl, n is 0, 1, 2, 3, 4, 5, 6, 7, 8, 9, 10, 11 or 12; and each of $X^1$ and $X^2$ is independently halogen or benzyl. Note that when n is 0, there is a direct —$CH_2$—$CH_2$— link between $N^1$ and $N^2$.

Methods to Prepare the Catalyst Compounds

In another aspect of the invention, there are provided various processes for synthesizing the complexes described herein.

Ligand Synthesis

The ligands described herein are generally prepared in multiple steps as shown in the scheme below:

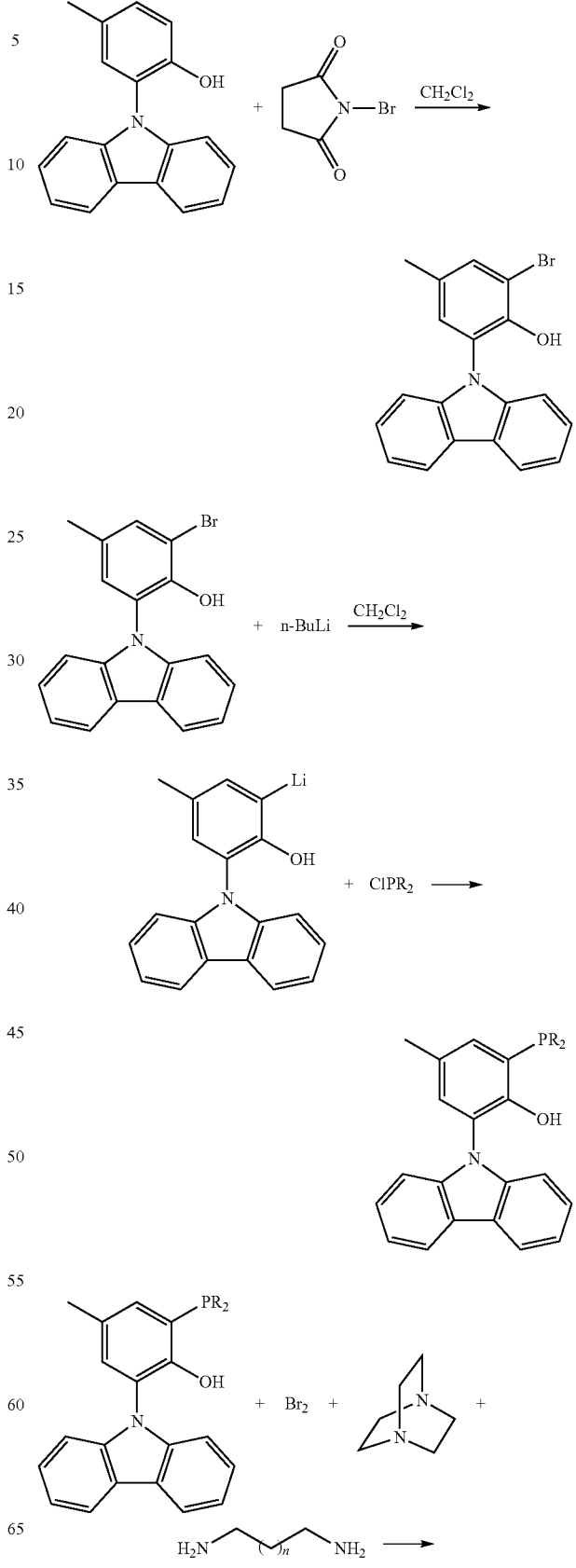

Scheme 1

-continued

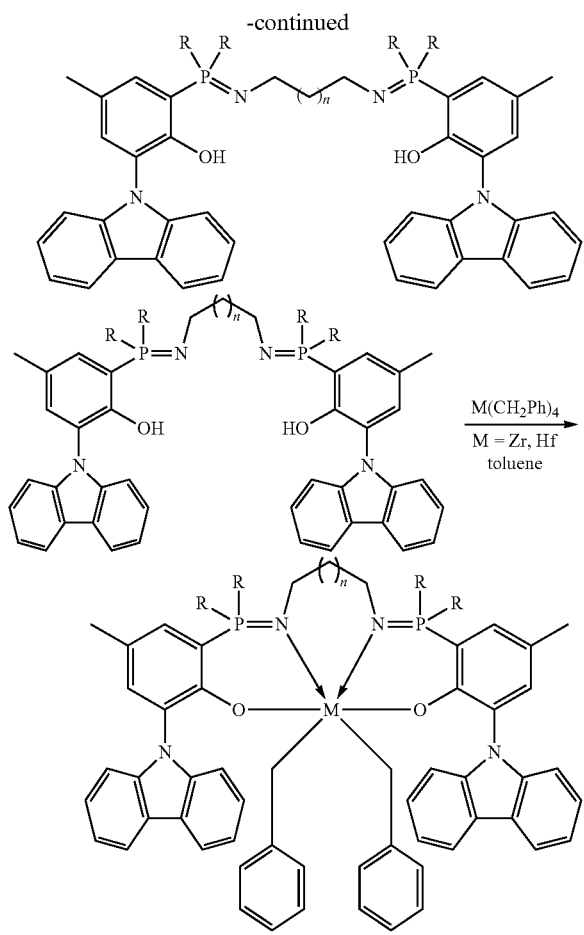

where R is as defined for $R^1$ above and n is 1, 2, 3, 4, 5, 6, 7, 8, 9, 10, 11 or 12.

The substituted phenol was brominated using N-bromosuccinamide and subsequently lithiated with n-butyl lithium. The chlorophosphane reagent was then added to generate the phosphorylated phenol. This step was followed by a Kisanov reaction with the diamine to give the phosphasalen compound. Subsequent metallation of the ligand with the metal tetrabenzyl complex affords the final catalyst precursor.

Activators

After the complexes have been synthesized, catalyst systems may be formed by combining the complexes with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator, such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When an alumoxane or modified alumoxane is used, the catalyst complex-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]$^+$[NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis (pentafluorophenyl)borate (i.e., [PhNMe$_2$H]B($C_6F_5$)$_4$) and N,N-dimethylanilinium tetrakis (heptafluoronaphthyl) borate, where Ph is phenyl, and Me is methyl.

Non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer, can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. The term non-coordinating anion includes ionic activators and Lewis acid activators.

Additionally, preferred activators useful herein include those described in U.S. Pat. No. 7,247,687 at column 169, line 50 to column 174, line 43, particularly column 172, line 24 to column 173, line 53.

Illustrative, but not limiting examples of boron compounds which may be used as an activating cocatalyst are the compounds described as (and particularly those specifically listed as) activators in U.S. Pat. Nos. 8,658,556 and/or 6,211,105, which are incorporated by reference herein.

Preferably, the NCA containing activator is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)

phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

When an NCA (such as an ionic or neutral stoichiometric activator) is used, the catalyst complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; or 1:1 to 1:1.2.

Alternately, a co-activator may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; or 1:10 to 2:1.

Supports

In some embodiments, the complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2/g$, a pore volume of 0.1-4.0 cc/g and an average particle size of 10-500 µm. Some embodiments select a surface area of 50-500 $m^2/g$, a pore volume of 0.5-3.5 cc/g, or an average particle size of 20-200 µm. Other embodiments select a surface area of 100-400 $m^2/g$, a pore volume of 0.8-3.0 cc/g, and an average particle size of 30-100 µm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

For purposes of this invention and the claims thereto, the term "continuous" means a system that operates without interruption or cessation. For example, a continuous process to produce a polymer would be one where the reactants are continually introduced into one or more reactors and polymer product is continually withdrawn.

For purposes of this invention and the claims thereto, a solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

For purposes of this invention and the claims thereto, a bulk polymerization preferably means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

"Catalyst activity" is a measure of how many grams of polymer (P) are produced using a polymerization catalyst comprising W mmol of transition metal (M), over a period of time of T hours; and may be expressed by the following formula: $P/(T \times W)$.

The inventive catalyst complexes described herein are useful in polymerizing unsaturated monomers conventionally known to undergo coordination catalyst-catalyzed polymerization such as solution, slurry, gas-phase, and high-pressure polymerization. Typically one or more of the complexes described herein, one or more activators, and one or more monomers are contacted to produce polymer. In certain embodiments, the complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Hydrogen may be used in the practice of this invention.

The present polymerization processes may be conducted under conditions preferably including a temperature of about 30° C. to about 200° C., preferably from 60° C. to 195° C., preferably from 75° C. to 190° C., preferably from 80° C. to 130° C. The process may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1,3,5,5-trimethylhexene-1, and 5-ethylnonene-1.

In some embodiments, the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, land 9-methyl-1,9-decadiene.

The polymerization of propylene or propylene-rich copolymers with ethylene is expected to produce polymer that has crystalline isotactic polypropylene runs. This is expected because the catalyst family has a seven-membered chelate ring, which effectively makes the catalyst $C_1$ symmetric (i.e. no symmetry) in use.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157; 5,241,025; PCT Publication Nos. WO-A-91/09882; WO-A-94/03506; WO-A-93/14132; and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes (methylalumoxane), aluminum oxides (e.g., bis(di-isobutylaluminum)oxide), and modified alumoxanes (e.g. MMAO-3A) also may be added in scavenging quantities with other activators such as $[Me_2HNPh]^+[B(pfp)_4]^-$ or $B(pfp)_3$ (perfluorophenyl=pfp=$C_6F_5$).

Polymer Products

While the molecular weight of the polymers produced herein can be influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC (as described below).

Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

In some embodiments herein, a multimodal polyolefin composition is produced, comprising a first polyolefin component and at least another polyolefin component, different from the first polyolefin component by molecular weight, preferably such that the GPC trace has more than one peak or inflection point.

The term "multimodal," when used to describe a polymer or polymer composition, means "multimodal molecular weight distribution," which is understood to mean that the Gel Permeation Chromatography (GPC) trace, plotted as Absorbance versus Retention Time (seconds), has more than one peak or inflection points. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition. Preferably, the Mw's of the polymers or polymer compositions differ by at least 10%, relative to each other, preferably by at least 20%, preferably at least 50%, preferably by at least 100%, preferably by a least 200%. Likewise, in a preferred embodiment, the Mw's of the polymers or polymer compositions differ by 10% to 10,000%, relative to each other, preferably by 20% to 1000%, preferably 50% to 500%, preferably by at least 100% to 400%, preferably 200% to 300%.

Unless otherwise indicated, measurements of the moments of molecular weight, i.e., weight average molecular weight (Mw), number average molecular weight (Mn), and z average molecular weight (Mz) are determined by Gel Permeation Chromatography (GPC) as described in Macromolecules, 2001, Vol. 34, No. 19, pg. 6812, which is fully incorporated herein by reference, including that, a High Temperature Size Exclusion Chromatograph (SEC, Waters Alliance 2000), equipped with a differential refractive index detector (DRI) equipped with three Polymer Laboratories PLgel 10 mm Mixed-B columns is used. The instrument is operated with a flow rate of 1.0 cm3/min, and an injection volume of 300 μL. The various transfer lines, columns and differential refractometer (the DRI detector) are housed in an oven maintained at 145 C. Polymer solutions are prepared by heating 0.75 to 1.5 mg/mL of polymer in filtered 1,2,4-Trichlorobenzene (TCB) containing ~1000 ppm of butylated hydroxy toluene (BHT) at 160° C. for 2 hours with continuous agitation. A sample of the polymer containing solution is injected into to the GPC and eluted using filtered 1,2,4-trichlorobenzene (TCB) containing ~1000 ppm of BHT. The separation efficiency of the column set is calibrated using a series of narrow MWD polystyrene standards reflecting the expected Mw range of the sample being analyzed and the exclusion limits of the column set. Seventeen individual polystyrene standards, obtained from Polymer Laboratories (Amherst, Mass.) and ranging from Peak Molecular Weight (Mp) ~580 to 10,000,000, were used to generate the calibration curve. The flow rate is calibrated for each run to give a common peak position for a flow rate marker (taken to be the positive inject peak) before determining the retention volume for each polystyrene standard. The flow marker peak position is used to correct the flow rate when analyzing samples. A calibration curve (log(Mp) vs. retention volume) is generated by recording the retention volume at the peak in the DRI signal for each PS standard, and fitting this data set to a 2nd-order polynomial. The equivalent polyethylene molecular weights are determined by using the Mark-Houwink coefficients shown in the below.

| Mark-Houwink coefficients | | |
|---|---|---|
| Material | K (dL/g) | α |
| PS | $1.75 \times 10^{-4}$ | 0.67 |
| PE | $5.79 \times 10^{-4}$ | 0.695 |

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC and have a multi-modal, preferably bimodal, Mw/Mn.

In embodiments of the invention, the polymer produced is an ethylene polymer or a propylene polymer.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

EXPERIMENTAL

$^1$H NMR spectroscopic data were acquired at 250, 400, or 500 MHz using solutions prepared by dissolving approximately 10 mg of a sample in either $C_6D_6$, $CD_2Cl_2$, $CDCl_3$, or D$_8$-toluene. The chemical shifts (δ) presented are relative to the residual protium in the deuterated solvent at 7.15, 5.32, 7.24, and 2.09 for $C_6D_6$, $CD_2Cl_2$, $CDCl_3$, and D8-toluene, respectively. For purposes of the claims 500 Mz and $CD_2Cl_2$ are used.

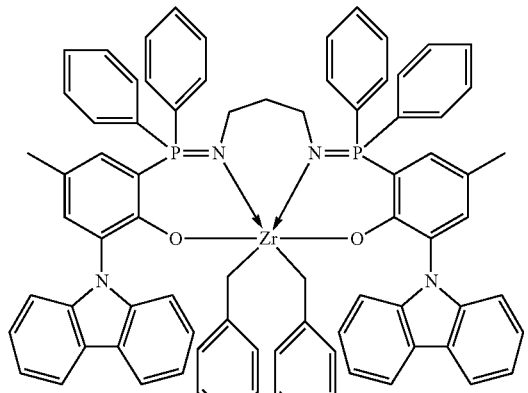

Catalyst 1-Zr

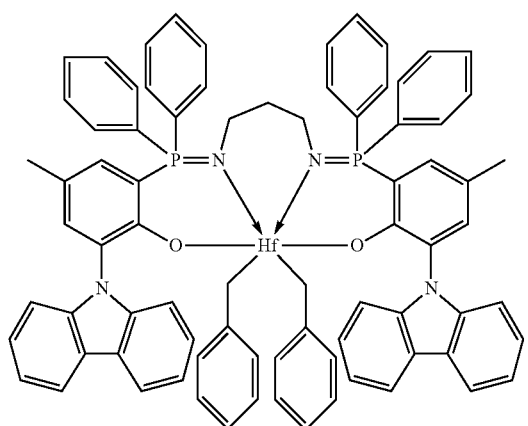

Catalyst 1-Hf

Synthesis of Ligands and Metal Complexes

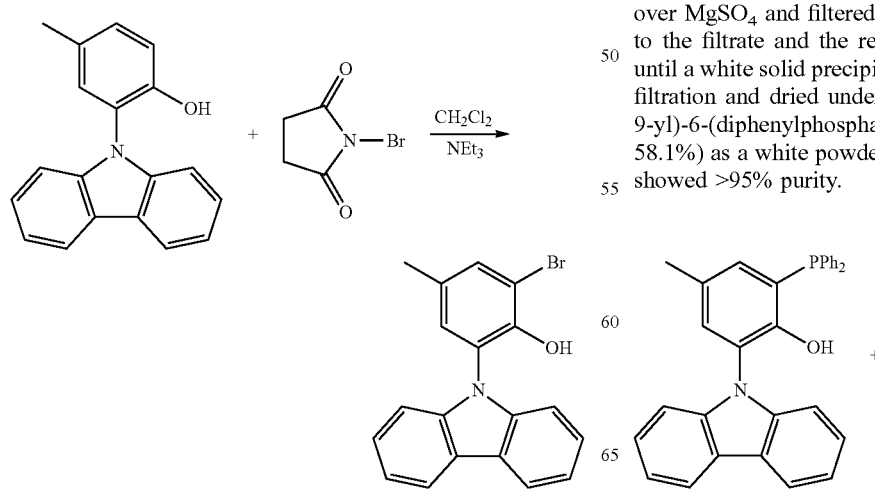

2-Bromo-6-(9H-carbazol-9-yl)-4-methylphenol 2-(9H-carbazol-9-yl)-4-methylphenol (3.124 g, 11.43 mmol) and trimethylamine (1.157 g, 11.43 mmol) were dissolved in dichloromethane (20 mL). A solution of N-bromosuccinamide (NBS, 2.238 g, 12.57 mmol) in dichloromethane (10 mL) was prepared then added dropwise to the phenol solution with stirring. The reaction was stirred for 30 minutes then quenched with 2 M HCl and washed with water (2×30 mL). The organic layer was collected, dried over $MgSO_4$, filtered and concentrated. The crude product was purified on Biotage SNAP Ultra column, eluting with a gradient of 5-20% ethyl acetate in hexane, to give 2-bromo-6-(9H-carbazol-9-yl)-4-methylphenol (3.548 g, 88.1%) as an off white solid.

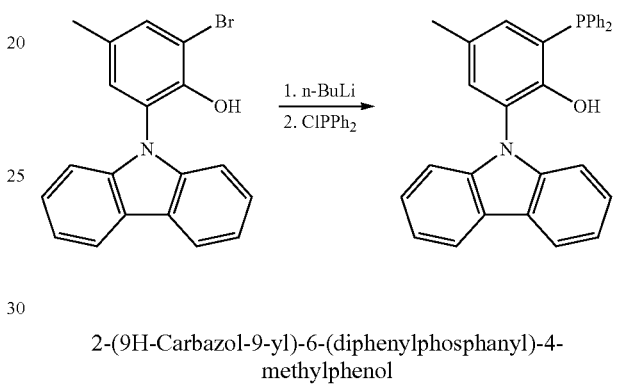

2-(9H-Carbazol-9-yl)-6-(diphenylphosphanyl)-4-methylphenol

In a nitrogen-purged drybox, 2-bromo-6-(9H-carbazol-9-yl)-4-methylphenol (0.984 g, 2.794 mmol) was dissolved in diethyl ether (100 mL) and the mixture was cooled to −78° C. 2.5 M n-butyllithium solution in hexane (2.40 mL, 6.007 mmol) was added to cooled solution and the contents were stirred for 30 minutes while warming to room temperature. The reaction was cooled again to −78° C. followed by addition of diphenylchlorophosphine (0.616 g, 2.794 mmol) and stirring for one hour. The mixture was removed from the cold bath and allowed to stir at room temperature overnight resulting in a white slurry. The reaction flask was removed from the drybox and the contents were washed with 0.1 M $NaH_2PO_4$ (2×50 mL). The organic layer was collected, dried over $MgSO_4$ and filtered. 20 mL cold methanol was added to the filtrate and the resulting solution was concentrated until a white solid precipitated. The solids were collected by filtration and dried under vacuum to give 2-(9H-carbazol-9-yl)-6-(diphenylphosphanyl)-4-methylphenol (0.743 g, 58.1%) as a white powder. $^1$H NMR analysis of the sample showed >95% purity.

-continued

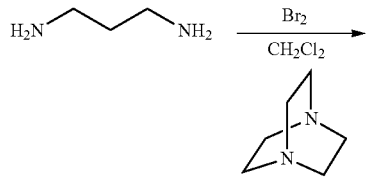

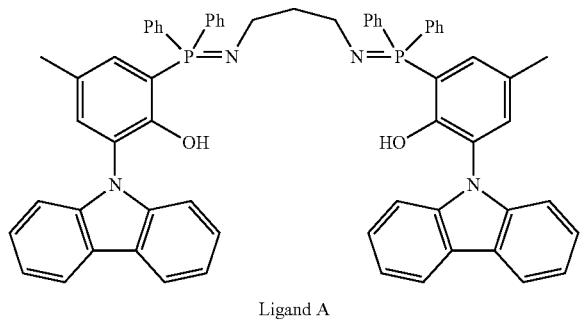

Ligand A 6,6'-((Propane-1,3-diylbis(azanylylidene))bis(diphenyl-l5-phosphanylylidene))bis(2-(9H-carbazol-9-yl)-4-methylphenol)

In a nitrogen-purged drybox, 2-(9H-carbazol-9-yl)-6-(diphenylphosphanyl)-4-methylphenol (0.309 g, 0.675 mmol) was dissolved in 20 mL of dichloromethane and cooled to −78° C. Bromine (0.108 g, 0.675 mmol) was added dropwise and the reaction was stirred for 1 hour while warming to room temperature. The solution was cooled again to −78° C. and 1,4-diazabicyclo [2.2.2]octane (DABCO, 0.038 g, 0.339 mmol) was added, followed by 1,3-propanediamine (0.025 g, 0.337 mmol). The flask was removed from the cold bath and allowed to stir at room temperature overnight. The solvent was removed under nitrogen flow and THF was added to the residue. The resulting mixture was filtered and concentrated to give a white solid which was further dried under vacuum. Yield: 0.337 g, 50.6%.

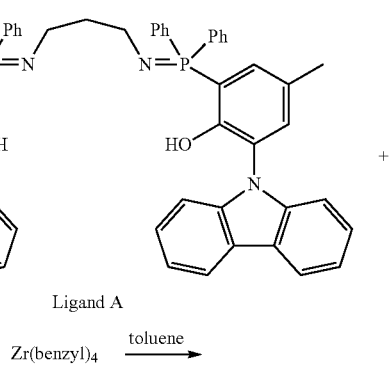

Ligand A

Zr(benzyl)₄ →^{toluene}

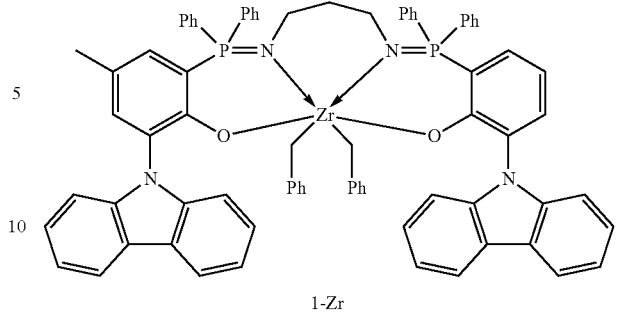

1-Zr

1-Zr

In a nitrogen-purged drybox, 4 mL toluene solutions of Ligand A (0.116 g, 0.117 mmol) and tetrabenzylzirconium (0.054 g, 0.117 mmol) were prepared separately. The tetrabenzylzirconium solution was slowly added to the stirring ligand solution. The resulting mixture was stirred for 1 hour. The toluene was removed and the residue taken up in pentane creating a yellow solid. The solid was filtered and dried under vacuum. Yield of solid: 0.112 g, 75.2%.

Ligand A

Hf(benzyl)₄ →^{toluene}

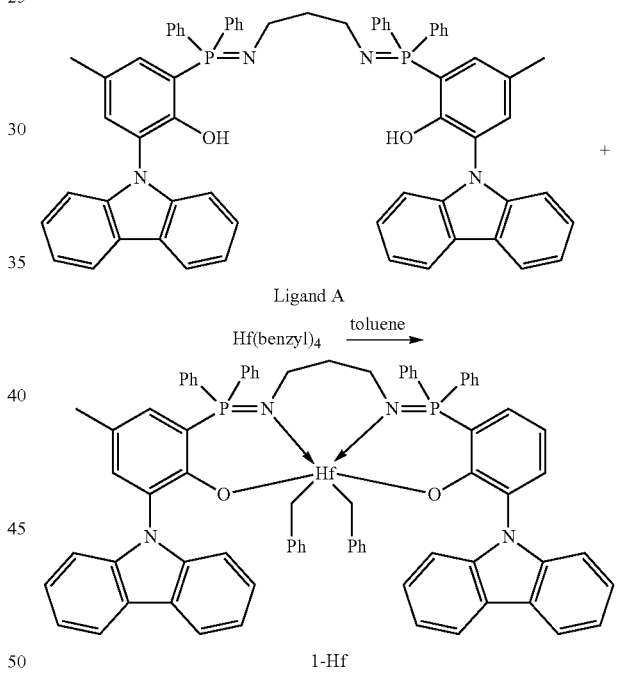

1-Hf

1-Hf

In a nitrogen-purged drybox, 4 mL toluene solutions of Ligand A (0.129 g, 0.130 mmol) and tetrabenzylhafnium (0.071 g, 0.130 mmol) were prepared separately. The tetrabenzylhafnium solution was slowly added to the stirring ligand solution. The resulting mixture was stirred for 1 hour. The toluene was removed and the residue taken up in pentane creating a white solid. The solid was filtered and dried under vacuum. Yield of solid: 0.142 g, 81.3%.

Olefin Polymerizations in Parallel Pressure Reactor

General Polymerization Procedures for Parallel Pressure Reactor.

Solvents, polymerization-grade toluene, and isohexane were supplied by ExxonMobil Chemical Company and purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

1-octene (C8) (98%, Aldrich Chemical Company) was dried by stirring over NaK overnight followed by filtration through basic alumina (Aldrich Chemical Company, Brockman Basic 1).

Polymerization-grade ethylene (C2) was used and further purified by passing the gas through a series of columns: 500 cc Oxyclear cylinder from Labclear (Oakland, Calif.) followed by a 500 cc column packed with dried 3 Å mole sieves (8-12 mesh; Aldrich Chemical Company) and a 500 cc column packed with dried 5 Å mole sieves (8-12 mesh; Aldrich Chemical Company).

Solutions of the metal complexes and activators were prepared in a drybox using toluene (ExxonMobil Chemical Company; anhydrous, stored under nitrogen; 98%). Concentrations were typically 0.2 mmol/L for the metal complexes and N,N-dimethyl anilinium tetrakis-pentafluorophenyl borate (Activator-1) and 0.5% w/w for methyl alumoxane (MAO).

For polymerization experiments with Activator-1 as activator, tri-n-octylaluminum (TNOAL, neat, AkzoNobel) or diisobutylaluminum oxide (DIBALO) was used as a scavenger. Concentration of the scavenger solution in toluene ranged from 0.5 to 2.0 mmol/L.

Polymerizations were carried out in a parallel, pressure reactor, as generally described in U.S. Pat. Nos. 6,306,658; 6,455,316; 6,489,168; PCT Publication No. WO 00/09255; and Murphy et al., J. Am. Chem. Soc., 2003, 125, pp. 4306-4317, each of which is fully incorporated herein by reference. The experiments were conducted in an inert atmosphere ($N_2$) drybox using autoclaves equipped with an external heater for temperature control, glass inserts (internal volume of reactor=23.5 mL for C2 and C2/C8; 22.5 mL for C3 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours. Although the specific quantities, temperatures, solvents, reactants, reactant ratios, pressures, and other variables are frequently changed from one polymerization run to the next, the following describes a typical polymerization performed in a parallel, pressure reactor.

Catalyst systems dissolved in solution were used in the polymerization examples below, unless specified otherwise.

Ethylene Homopolymerization (HDPE) and Ethylene-Octene Copolymerization (EO).

A pre-weighed glass vial insert and disposable stirring paddle were fitted to each reaction vessel of the reactor, which contains 48 individual reaction vessels. The reactor was then closed and purged with ethylene. Each vessel was charged with enough solvent (typically isohexane) to bring the total reaction volume, including the subsequent additions, to the desired volume, typically 5 mL. 1-octene, if required, was injected into the reaction vessel and the reactor was heated to the set temperature and pressurized to the predetermined pressure of ethylene, while stirring at 800 rpm. The aluminum and/or zinc compound in toluene was then injected as scavenger and/or chain transfer agent followed by addition of the activator solution (typically 1.0-1.2 molar equivalents of N,N-dimethyl anilinium tetrakis-pentafluorophenyl borate—Activator-1).

The catalyst solution (typically 0.020-0.080 umol of metal complex) was injected into the reaction vessel and the polymerization was allowed to proceed until a pre-determined amount of ethylene (quench value typically 20 psi) had been used up by the reaction. Alternatively, the reaction may be allowed to proceed for a set amount of time (maximum reaction time typically 30 minutes). Ethylene was added continuously (through the use of computer controlled solenoid valves) to the autoclaves during polymerization to maintain reactor gauge pressure (+/−2 psig) and the reactor temperature was monitored and typically maintained within +/−1° C. The reaction was quenched by pressurizing the vessel with compressed air. After the reactor was vented and cooled, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine percent octene incorporation, and by DSC (see below) to determine melting point (Tm).

For polymerizations using MAO as activator (typically 100 to 1000 molar equivalents), the MAO solution was injected into the reaction vessel after the addition of 1-octene and prior to heating the vessel to the set temperature and pressurizing with ethylene. No additional aluminum reagent was used as scavenger during these runs.

Equivalence is determined based on the mole equivalents relative to the moles of the transition metal in the catalyst complex.

Polymer Characterization.

Polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 am, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.28 mg/mL and 400 uL of a polymer solution was injected into the system. The concentration of the polymer in the eluent was monitored using an evaporative light scattering detector. The molecular weights presented are relative to linear polystyrene standards and are uncorrected, unless indicated otherwise.

Differential Scanning Calorimetry (DSC) measurements were performed on a TA-Q100 instrument to determine the melting point (Tm) of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period.

The weight percent of ethylene incorporated in polymers was determined by rapid FT-IR spectroscopy on a Bruker Equinox 55+ IR in reflection mode. Samples were prepared in a thin film format by evaporative deposition techniques. FT-IR methods were calibrated using a set of samples with a range of known wt % ethylene content. For ethylene-1- octene copolymers, the wt % octene in the copolymer was determined via measurement of the methyl deformation band at ~1375 cm$^{-1}$. The peak height of this band was normalized by the combination and overtone band at ~4321 cm$^{-1}$, which corrects for path length differences.

wherein M is a Group 4 metal;
$N^1$ and $N^2$ are nitrogen;
O is oxygen;
P is phosphorus;

Ethylene/Octene Polymerization Using 1-Zr

| Example | Activator | Scavenger | umol | C8 uL | T (° C.) | P setpt (psi) | 1-Zr umol | time (s) | yield (g) | activity (kg/mmol-hr) | Mw (kg/mol) | Mn (kg/mol) | Mw/Mn | wt % C8 | Tm (° C.) |
|---|---|---|---|---|---|---|---|---|---|---|---|---|---|---|---|
| 1 | Activator-1 | DIBALO | 1 | 180 | 70 | 150 | 0.04 | 1800.2 | 0.005 | 0.2 | — | — | — | — | — |
| 2 | | | | | | | 0.10 | 1801.3 | 0.012 | 0.2 | 483 | 20 | 24.7 | 0.8 | 129.9 |
| 3 | MAO | — | — | 180 | 70 | 150 | 0.04 | 1800.4 | 0.009 | 0.4 | — | — | — | — | — |
| 4 | | | | | | | 0.04 | 1800.2 | 0.010 | 0.5 | 1064 | 13 | 81.1 | 1.9 | 129.0 |
| 5 | | | | 180 | 70 | 150 | 0.04 | 1800.1 | 0.011 | 0.5 | 1333 | 27 | 49.1 | 2.9 | 128.3 |
| 6 | | | | | | | 0.10 | 1800.6 | 0.021 | 0.4 | 1810 | 58 | 31.3 | 0.7 | 131.6 |
| 7 | | | | 180 | 70 | 150 | 0.10 | 1800.4 | 0.024 | 0.5 | 1904 | 95 | 20.1 | 0.2 | 132.2 |
| 8 | | | | | | | 0.10 | 1800.9 | 0.022 | 0.4 | 1190 | 13 | 94.0 | 2.6 | 135.6 |
| 9 | Activator-1 | TNOAL | 0.5 | 100 | 100 | 135 | 0.15 | 1800.8 | 0.023 | 0.3 | 228 | 14 | 16.9 | 0.2 | 128.1 |
| 10 | | | | | | | 0.15 | 1800.8 | 0.023 | 0.3 | 328 | 12 | 27.5 | 1.9 | 128.4 |
| 11 | | TNOAL | 1 | 100 | 100 | 135 | 0.15 | 1801.0 | 0.019 | 0.3 | 355 | 10 | 37.1 | 0.9 | 127.3 |
| 12 | | | | | | | 0.15 | 1800.8 | 0.019 | 0.3 | 415 | 10 | 40.2 | 3.3 | 128.2 |
| 13 | | DIBALO | 1 | 100 | 100 | 135 | 0.15 | 1800.9 | 0.030 | 0.4 | 218 | 15 | 14.7 | 0.6 | 127.9 |
| 14 | | | | | | | 0.15 | 1800.7 | 0.028 | 0.4 | 175 | 14 | 12.4 | 1.2 | 128.4 |
| 15 | MAO | — | — | 100 | 100 | 135 | 0.15 | 1418.5 | 0.045 | 0.8 | 650 | 20 | 32.9 | 1.4 | 127.0 |
| 16 | | | | | | | 0.15 | 1182.9 | 0.032 | 0.6 | 766 | 29 | 26.1 | 1.6 | 128.0 |
| 17 | Activator-1 | TNOAL | 0.5 | 0 | 80 | 95 | 0.15 | 1800.0 | 0.012 | 0.2 | 605 | 16 | 37.9 | 0.0 | 132.5 |
| 18 | | | | | | | 0.15 | 1801.3 | 0.011 | 0.1 | 700 | 14 | 49.4 | 0.0 | 132.6 |
| 19 | | TNOAL | 0.5 | 0 | 100 | 135 | 0.15 | 1800.2 | 0.022 | 0.3 | 344 | 11 | 31.9 | 0.0 | 131.1 |
| 20 | | | | | | | 0.15 | 985.1 | 0.014 | 0.3 | 245 | 10 | 25.0 | 0.0 | 130.9 |
| 21 | | TNOAL | 1 | 0 | 80 | 95 | 0.15 | 1801.0 | 0.011 | 0.1 | 892 | 10 | 85.4 | 0.0 | 131.8 |
| 22 | | | | | | | 0.15 | 1800.8 | 0.011 | 0.1 | 714 | 10 | 72.2 | 0.0 | 131.8 |
| 23 | | TNOAL | 1 | 0 | 100 | 135 | 0.15 | 1800.2 | 0.018 | 0.2 | 237 | 8 | 29.7 | 0.0 | 130.2 |
| 24 | | | | | | | 0.15 | 1740.8 | 0.016 | 0.2 | 364 | 9 | 38.7 | 0.0 | 130.2 |
| 25 | | DIBALO | 1 | 0 | 80 | 95 | 0.15 | 1495.5 | 0.013 | 0.2 | 492 | 22 | 22.7 | 0.0 | 134.2 |
| 26 | | | | | | | 0.15 | 1800.4 | 0.014 | 0.2 | 443 | 20 | 22.2 | 0.0 | 132.9 |
| 27 | | DIBALO | 1 | 0 | 100 | 135 | 0.15 | 1800.9 | 0.027 | 0.4 | 281 | 15 | 18.3 | 0.0 | 131.3 |
| 28 | | | | | | | 0.15 | 351.6 | 0.010 | 0.7 | 224 | 10 | 23.1 | 0.0 | 130.6 |
| 29 | MAO | — | — | 0 | 80 | 95 | 0.15 | 1241.4 | 0.038 | 0.7 | 1292 | 13 | 98.9 | 0.0 | 133.0 |
| 30 | | | | | | | 0.15 | 1216.4 | 0.035 | 0.7 | 1353 | 19 | 72.8 | 0.0 | 134.0 |
| 31 | | | | 0 | 100 | 135 | 0.15 | 938.9 | 0.033 | 0.8 | 676 | 17 | 38.8 | 0.0 | 132.8 |
| 32 | | | | | | | 0.15 | 1263.6 | 0.046 | 0.9 | 806 | 20 | 41.2 | 0.0 | 133.4 |

Activator-1 = N,N-dimethyl anilinium tetrakis-pentafluorophenyl borate.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element, or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A transition metal complex represented by the formula:

(I)

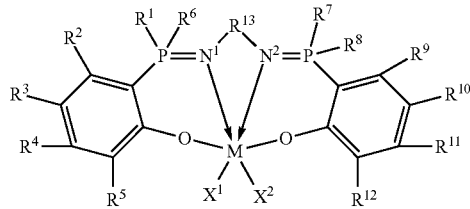

each of $X^1$ and $X^2$ is, independently, a univalent $C_1$ to $C_{20}$ hydrocarbyl radical, a functional group comprising elements from Groups 13 to 17, or $X^1$ and $X^2$ join together to form a $C_4$ to $C_{62}$ cyclic, polycyclic ring, or heterocyclic ring structure;

each of $R^1$, $R^2$, $R^3$, $R^4$, $R^5$, $R^6$, $R^7$, $R^8$, $R^9$, $R^{10}$, $R^{11}$ and $R^{12}$ is, independently, hydrogen, a $C_1$-$C_{40}$ hydrocarbyl radical, a $C_1$-$C_{40}$ substituted hydrocarbyl radical, a functional group comprising elements from Groups 13 to 17, two or more of $R^1$, $R^2$, $R^3$, $R^4$, $R^5$, $R^6$, $R^7$, $R^8$, $R^9$, $R^{10}$, $R^{11}$, and $R^{12}$ optionally join together to form a $C_4$ to $C_{62}$ cyclic, polycyclic, or heterocyclic ring structure, or a combination thereof; and $R^{13}$ is a divalent $C_2$-$C_{20}$ hydrocarbyl radical or divalent substituted $C_1$-$C_{20}$ hydrocarbyl radical comprising a portion that comprises a linking backbone comprising from 2 to 18 carbon atoms linking $N^1$ and $N^2$.

2. The complex of claim 1, wherein M is Zr or Hf.

3. The complex of claim 1, wherein $X^1$ and $X^2$ are independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido.

4. The complex of claim 1, wherein $R^{13}$ is a divalent $C_2$-$C_{10}$ hydrocarbyl radical or divalent substituted $C_2$-$C_{10}$ hydrocarbyl radical comprising a portion that comprises a linker backbone comprising from 2 to 10 carbon atoms linking or bridging $N^1$ and $N^2$.

5. The complex of claim 1, wherein $R^{13}$ comprises a C2 to C8 hydrocarbyl.

6. The complex of claim 1, wherein $R^{13}$ is —CH$_2$CH$_2$CH$_2$—.

7. The complex of claim 1, wherein each of $R^1$, $R^2$, $R^3$, $R^4$, $R^5$, $R^6$, $R^7$, $R^8$, $R^9$, $R^{10}$, $R^{11}$ and $R^{12}$ is, independently, a $C_1$-$C_{20}$ hydrocarbyl radical.

8. The complex of claim 1, wherein, each of $R^1$, $R^2$, $R^3$, $R^4$, $R^6$, $R^7$, $R^8$, $R^9$, $R^{10}$, and $R^{11}$ is, independently, $C_1$-$C_{10}$ alkyl or aromatic radical.

9. The complex of claim 1, wherein each of $R^5$ and $R^{12}$ is, independently, $C_1$-$C_{20}$ alkyl or aromatic radical.

10. The complex of claim 1, wherein each of $R^5$ and $R^{12}$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, adamantyl, substituted adamantyl, cyclohexyl, substituted cyclohexyl phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, and substituted indenyl.

11. The complex of claim 1, wherein one or both of $R^5$ and $R^{12}$ is selected from the group consisting of methyl, tert-butyl, adamantyl, substituted adamantyl, cyclohexyl, substituted cyclohexyl, phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, and substituted indenyl.

12. The complex of claim 1, wherein $R^{13}$ is a divalent $C_2$-$C_{20}$ hydrocarbyl radical or divalent substituted $C_2$-$C_{20}$ hydrocarbyl radical comprising a portion that comprises a linking backbone comprising from 2 to 18 carbon atoms linking $N^1$ and $N^2$.

13. The complex of claim 1, wherein $R^{13}$ is a divalent $C_3$ hydrocarbyl radical or divalent substituted $C_2$-$C_{20}$ hydrocarbyl radical linking $N^1$ and $N^2$.

14. The complex of claim 1, wherein the transition metal complex is represented by the formula:

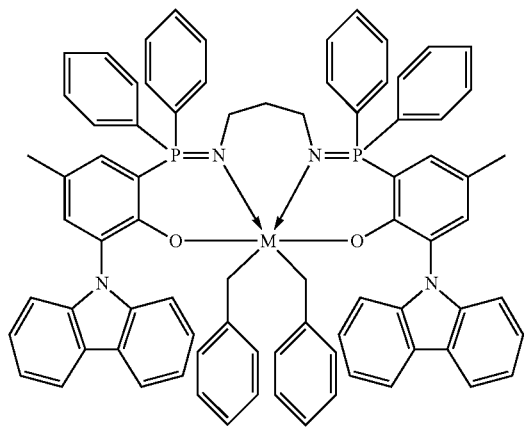

where M is Hf or Zr.

15. A catalyst system comprising an activator and the transition metal complex of claim 1.

16. The catalyst system of claim 15, wherein two or more transition metal complexes are present.

17. The catalyst system of claim 15, wherein the activator is an alumoxane.

18. The catalyst system of claim 15, wherein the activator is a non-coordinating anion.

19. The catalyst system of claim 15, wherein the transition metal complex and/or the activator is supported.

20. A polymerization process to produce polyolefin comprising contacting one or more olefin monomers with the catalyst system of claim 15 and obtaining olefin polymer.

21. The process of claim 20, wherein the monomers comprise ethylene.

22. The process of claim 20, wherein the monomers comprise propylene.

23. The process of claim 20, wherein the polymerization process is a solution process.

24. The process of claim 20, wherein the polyolefin produced is an ethylene polymer.

25. The process of claim 20, wherein the polyolefin produced is propylene polymer.

26. The catalyst system of claim 15, wherein M is Zr or Hf; wherein $X^1$ and $X^2$ are independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido; and wherein $R^{13}$ is a divalent $C_2$-$C_{10}$ hydrocarbyl radical or divalent substituted $C_2$-$C_{10}$ hydrocarbyl radical comprising a portion that comprises a linker backbone comprising from 2 to 10 carbon atoms linking or bridging $N^1$ and $N^2$.

27. The catalyst system of claim 15, wherein $R^{13}$ comprises a $C_2$ to $C_8$ hydrocarbyl and each of $R^1$, $R^2$, $R^3$, $R^4$, $R^5$, $R^6$, $R^7$, $R^8$, $R^9$, $R^{10}$, $R^{11}$ and $R^{12}$ is, independently, a $C_1$-$C_{20}$ hydrocarbyl radical.

28. The catalyst system of claim 15, wherein each of $R^1$, $R^2$, $R^3$, $R^4$, $R^6$, $R^7$, $R^8$, $R^9$, $R^{10}$, and $R^{11}$ is, independently, $C_1$-$C_{10}$ alkyl or aromatic radical and each of $R^5$ and $R^{12}$ is, independently, $C_1$-$C_{20}$ alkyl or aromatic radical.

29. The catalyst system of claim 15, wherein each of $R^5$ and $R^{12}$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, adamantyl, substituted adamantyl, cyclohexyl, substituted cyclohexyl phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, and substituted indenyl.

30. The catalyst system of claim 15, wherein $R^{13}$ is a divalent $C_2$-$C_{20}$ hydrocarbyl radical or divalent substituted $C_2$-$C_{20}$ hydrocarbyl radical comprising a portion that comprises a linking backbone comprising from 2 to 18 carbon atoms linking $N^1$ and $N^a$.

31. The catalyst system of claim 15, wherein $R^{13}$ is a divalent $C_3$ hydrocarbyl radical or divalent substituted $C_2$-$C_{20}$ hydrocarbyl radical linking $N^1$ and $N^2$.

32. A polymerization process to produce polyolefin comprising contacting one or more olefin monomers with the catalyst system of claim 26 and obtaining olefin polymer.

33. A polymerization process to produce polyolefin comprising contacting one or more olefin monomers with the catalyst system of claim 27 and obtaining olefin polymer.

34. A polymerization process to produce polyolefin comprising contacting one or more olefin monomers with the catalyst system of claim 28 and obtaining olefin polymer.

35. A polymerization process to produce polyolefin comprising contacting one or more olefin monomers with the catalyst system of claim 29 and obtaining olefin polymer.

36. A polymerization process to produce polyolefin comprising contacting one or more olefin monomers with the catalyst system of claim 30 and obtaining olefin polymer.

37. A polymerization process to produce polyolefin comprising contacting one or more olefin monomers with the catalyst system of claim 31 and obtaining olefin polymer.

* * * * *